United States Patent
Holmes et al.

(10) Patent No.: US 7,105,338 B1
(45) Date of Patent: Sep. 12, 2006

(54) MOTORIZED TURNTABLE FOR PETRI DISH

(76) Inventors: Richard Holmes, 775 E. Blithdale Ave., #400, Mill Valley, CA (US) 94941; Richard G. Halstead, 4623 Fairway Dr., Rohnert Park, CA (US) 94928; Richard G. Malmquist, 614 Galland St., Petaluma, CA (US) 94952; Douglass M. Nolte, 43 Millbrae Ave., San Anselmo, CA (US) 94960

( * ) Notice: Subject to any disclaimer, the term of this patent is extended or adjusted under 35 U.S.C. 154(b) by 630 days.

(21) Appl. No.: 10/262,995

(22) Filed: Oct. 2, 2002

Related U.S. Application Data

(60) Provisional application No. 60/329,866, filed on Oct. 17, 2001.

(51) Int. Cl.
*C12M 1/22* (2006.01)
*C12M 1/34* (2006.01)

(52) U.S. Cl. .............................. 435/286.3; 435/287.3; 435/309.3; 108/20; 248/349.1; 369/266; 369/270.1

(58) Field of Classification Search ............ 435/286.2, 435/286.3, 287.3, 309.1, 309.3; 192/84.3, 192/53.2; 248/349.1; 108/20; 476/64; 369/266, 369/270.1
See application file for complete search history.

(56) References Cited

U.S. PATENT DOCUMENTS

| | | | |
|---|---|---|---|
| 1,368,587 A * | 2/1921 | Cecil | 476/11 |
| 2,485,848 A | 10/1949 | Sharp | |
| 2,902,741 A * | 9/1959 | Hankin, Jr. | 425/459 |
| 3,760,745 A | 9/1973 | MacManus | |
| 3,894,830 A * | 7/1975 | Edwards | 425/459 |
| 3,965,762 A * | 6/1976 | Nessel | 476/11 |
| 4,170,861 A | 10/1979 | Snyder et al. | |
| 4,222,577 A * | 9/1980 | Giffin | 279/114 |
| 4,239,009 A | 12/1980 | Cunningham | |
| 4,273,877 A * | 6/1981 | Anagnostopoulos | 435/286.3 |
| 4,555,990 A | 12/1985 | Egawa | |
| 4,788,397 A | 11/1988 | Danley | |
| 5,020,297 A | 6/1991 | Borie et al. | |
| 5,149,043 A | 9/1992 | Grundmann | |
| 5,239,892 A | 8/1993 | Sakai | |
| 5,555,709 A | 9/1996 | Savigny et al. | |
| 5,582,112 A | 12/1996 | Huang | |
| 5,831,182 A * | 11/1998 | Swenson | 73/863.22 |
| 5,937,764 A | 8/1999 | Olivier | |

FOREIGN PATENT DOCUMENTS

| JP | 61142566 A * | 6/1986 |
|---|---|---|
| JP | 090236751 A * | 9/1997 |

* cited by examiner

*Primary Examiner*—William H. Beisner
(74) *Attorney, Agent, or Firm*—Mark J. Spolyar

(57) ABSTRACT

Improvements to turntables that facilitate inoculation of petri dishes. In one embodiment, the present invention is a motorized turntable for a petri dish that allows the user to use both hands for inoculation of the petri dish. In another embodiment, the present invention features an improved upper plate for a petri dish turntable that allows the user to more easily remove the petri dish from the upper plate after inoculation. In another embodiment, the present invention provides an apparatus for rotating a conventional turntable for petri dishes.

17 Claims, 5 Drawing Sheets

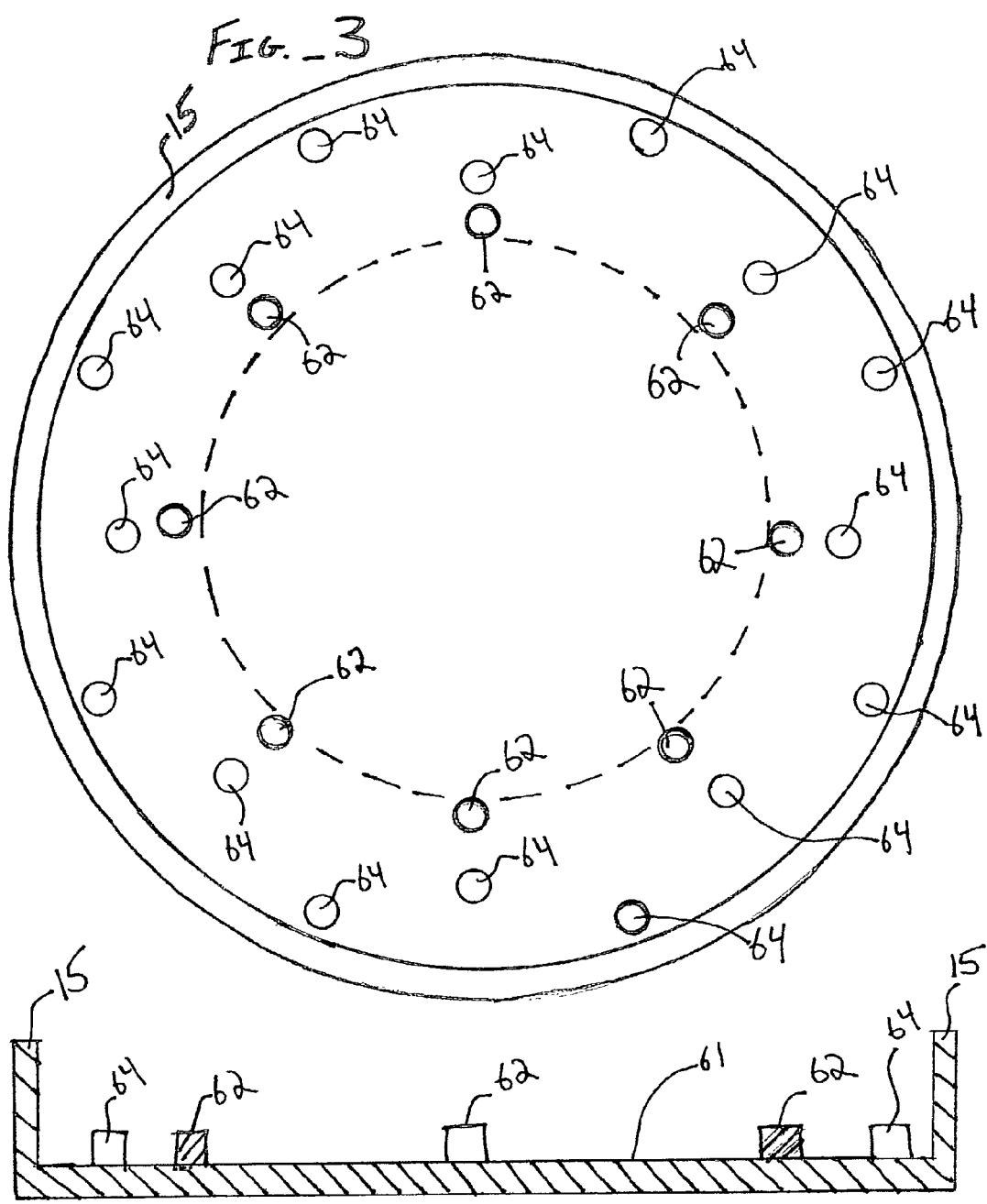

FIG._6

MOTORIZED TURNTABLE FOR PETRI DISH

RELATED APPLICATION

The present application claims priority from provisional application Ser. No. 60/329,866 filed Oct. 17, 2001.

FIELD OF THE INVENTION

The present invention relates to petri dishes and, more particularly, to apparatuses that rotate, and/or improvements to, turntables that facilitate inoculation of petri dishes.

BACKGROUND OF THE INVENTION

Petri dishes are small circular boxes typically made of transparent plastic material, containing a nutrient such as a mixture of gelose and distilled water. They are used as a development medium for cultures containing microorganisms and are used in large numbers in analysis laboratories, in particular in medical research and in industry.

Manually operated turntables for petri dishes are known. Such turntables include a base and an upper plate rotatably mounted on the base. The upper plate is configured with a rim extending around the perimeter of the upper plate, and is generally configured to match the bottom surface of a petri dish, to hold a petri dish in place. To inoculate a petri dish with bacteria or other microorganism, the user must manually rotate the upper plate with one hand, while handling filling equipment with the other—often times a cumbersome and awkward process.

As discussed above, prior art turntables feature an upwardly extending lip that holds the petri dish in place. This lip, however, inhibits removal of the petri dish from the turn table since the lip extends almost to the upper edge of the petri dish. This configuration often forces lab workers to contact the inner surfaces of the petri dish to extract it from the turntable which creates the risk of contamination.

In light of the foregoing, a need exists in the art for turntables for petri dishes, or other apparatuses, that address the above-noted problems.

SUMMARY OF THE INVENTION

The present invention provides apparatuses that rotate, and improvements to, petri dish turntables that facilitate inoculation of petri dishes. In one embodiment, the present invention is a motorized turntable for a petri dish that allows the user to use both hands for inoculation of the petri dish. In another embodiment, the present invention features an improved upper plate for a petri dish turntable that allows the user to more easily remove the petri dish from the upper plate after inoculation. In another embodiment, the present invention provides an apparatus for rotating a conventional turntable for petri dishes.

DESCRIPTION OF THE DRAWINGS

FIG. 3 is a top plan view of a turntable according to another embodiment of the present invention.

FIG. 4 is a sectional plan view of the turntable depicted in FIG. 3.

DESCRIPTION OF PREFERRED EMBODIMENT(S)

Figure 1:
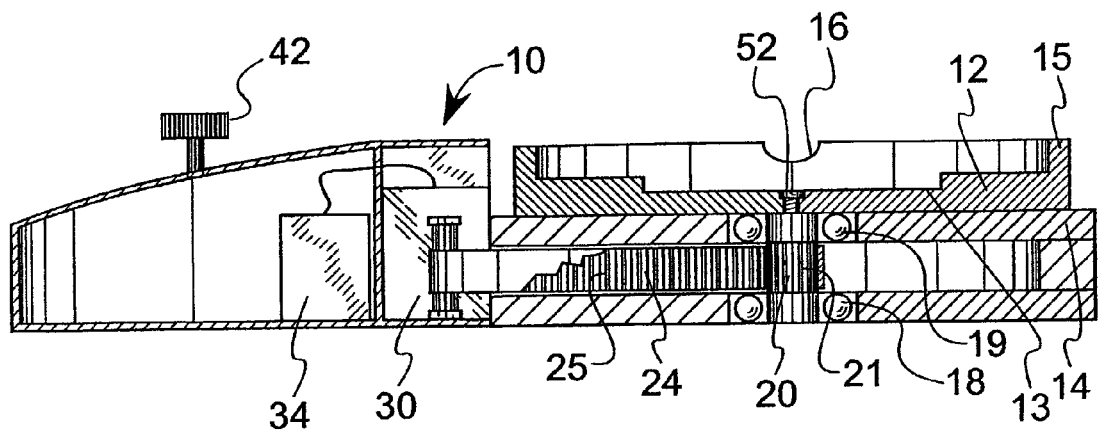
FIG. 1 is a cross sectional view of a motorized turntable according to one embodiment of the present invention.
Figure 2:
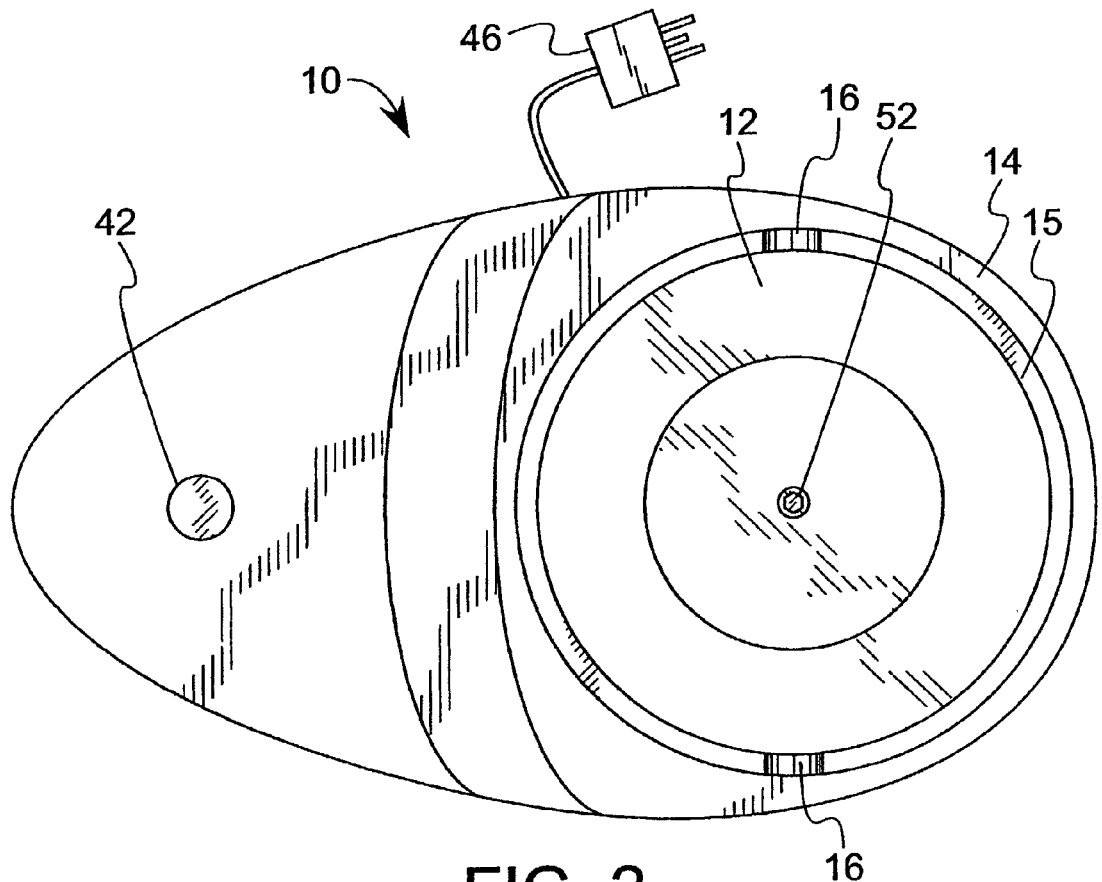
FIG. 2 is a top plan view of a motorized turntable according to one embodiment of the present invention.

FIGS. 1 and 2 illustrate an embodiment of a motorized turntable assembly 10 for a petri dish. Turntable assembly 10, in one embodiment, comprises turntable 12 rotatably mounted in base 14, as more fully described below. To rotate turntable 12, turntable assembly 10 includes motor 30, drive belt 24, shaft 20 and ball bearings 18 and 19. As FIG. 1 shows, recessed screw 52 secures turntable 12 to shaft 20. Shaft 20 is rotatably mounted in base 14 with ball bearings 18 and 19 to allow for rotation of turntable 12 about its central axis.

Motor 30 includes drive belt 24 extending around shaft 20. In one embodiment, drive belt 24 includes teeth 25 that substantially match and, thus, engage mating teeth 21 in shaft 20. Drive belt 24 is under sufficient tension to effectuate rotation of shaft 20 when motor 30 is powered. Other motor/drive assemblies are possible, as well. For example, the motor/drive assembly may comprise a gear drive system, rather than a drive belt. Another embodiment may include a chain drive system. Motor 30 can be any suitable motor. In one embodiment, motor 30 is an electronic DC motor powered by electrical power assembly 34.

In one embodiment, power assembly 34 includes a rechargeable battery, such as a Nickel-Cadmium or Lithium-Ion battery, a charge controller, and an electrical plug 46. When electrical plug 46 is plugged in to a suitable electric socket, the charge controller converts A/C power to DC to allow for recharging of the battery. In one embodiment, the charge controller also monitors the charge of the battery to turn charging on and off. In one embodiment, the charge controller simultaneously provides power to motor 30, while charging the battery. The battery also allows for operation of turntable assembly 10 when it is not plugged into an electrical outlet.

The upper surface of turntable 12 is dimensioned to receive standard-sized petri dishes (e.g., 150 mm (diameter)×15 mm (height)), such that the central axis of turntable 12 substantially corresponds to the central axis of the petri dish when it is placed within outer rim 15. Turntable 12, in one embodiment, includes outer rim 15 and recessed surface 13 accommodating different sizes of petri dish. Larger petri-dishes (e.g., 150 mm diameter petri dishes) extend to outer rim 15, while smaller dishes (e.g., 100 mm diameter petri dishes) lie within recessed surface 13 and engaged by the vertical edge provided thereby. As FIGS. 1 and 2 show, turntable 12 includes at least one notch (e.g., opposing notches 16) in outer rim 15 that facilitates placement and removal of petri dishes on turntable 12 without having to contact the inner surface of the petri dish.

Switch knob 42, in one embodiment, controls operation of motor 30 to selectively rotate turntable 12. Many switch and motor configurations are possible. For example, motor 30 can be a single speed motor, a dual speed motor, or a variable speed motor. Moreover, motor 30 may include a clutch assembly that allows the user to disengage the clutch and manually rotate turntable 12. Similar to a volume control knob on a car radio, switch knob 42 may control the power to motor 30 and, thereby, the speed of rotation of turntable 12. In addition, motor 30 can be configured to rotate turntable 12 in a counter-clockwise direction, a clockwise direction, or both selectively. In addition, switch knob 42 may be replaced or supplemented with a foot-operated pedal, attached to base 14 via a cord, which the user depresses to effectuate rotation of turntable 12. In one embodiment, the foot-operated pedal may be a rheostat-based device allowing for control of the rotational speed of turntable 12.

In use, a user places a petri dish in turntable 12 and turns switch knob 42 to effect rotation of the petri-dish. With embodiments involving dual or variable speed motors, the user controls the speed of rotation by turning switch knob 42 further to increase rotation speed and back to decrease rotation speed. While the petri dish rotates, the user's hands are free to inoculate the petri dish or perform any other desired operation.

In addition, FIGS. 3 and 4 illustrate an alternative embodiment of turntable 12 for use in connection with the present invention. As FIGS. 3 and 4 shows, turntable 12 includes a plurality of rubber knobs, instead of a recessed surface, to accommodate petri dishes of different sizes. Specifically, turntable 12 includes a first set of rubber knobs 62 arranged in a circular pattern such that a smaller diameter petri dish (e.g., 100 mm diameter) rests on surface 61 and is held in place by rubber knobs 62—that is, the outer surface (depicted by the dash line) of the petri dish extends to and/or contacts rubber knobs 62. Of course, other patterns of rubber knobs 62, such as a triangular pattern of three rubber knobs 62 can be used. Rubber knobs 62, in one embodiment, are about 4 mm in diameter and about 4–8 mm in height (preferably, rubber knobs 62 do not extend beyond the upper edge of the petri dish). Of course, the exact dimensions of rubber knobs 62, as well as their placement on turntable 12, are a matter of design choice. Turntable 12, in one embodiment, further includes additional rubber knobs 64 (in one embodiment, of the same height as rubber knobs 62) disposed outside of the first pattern of rubber knobs 62, such as along outer rim 15. Accordingly, a larger diameter petri dish (e.g., 150 mm diameter) rests on rubber knobs 62 and 64 and within outer rim 15. Lastly, although use of rubber is preferred as the friction between the knobs and the petri dish further stabilize the dish; other materials can be used, such as metal, plastic and the like.

Figure 5:
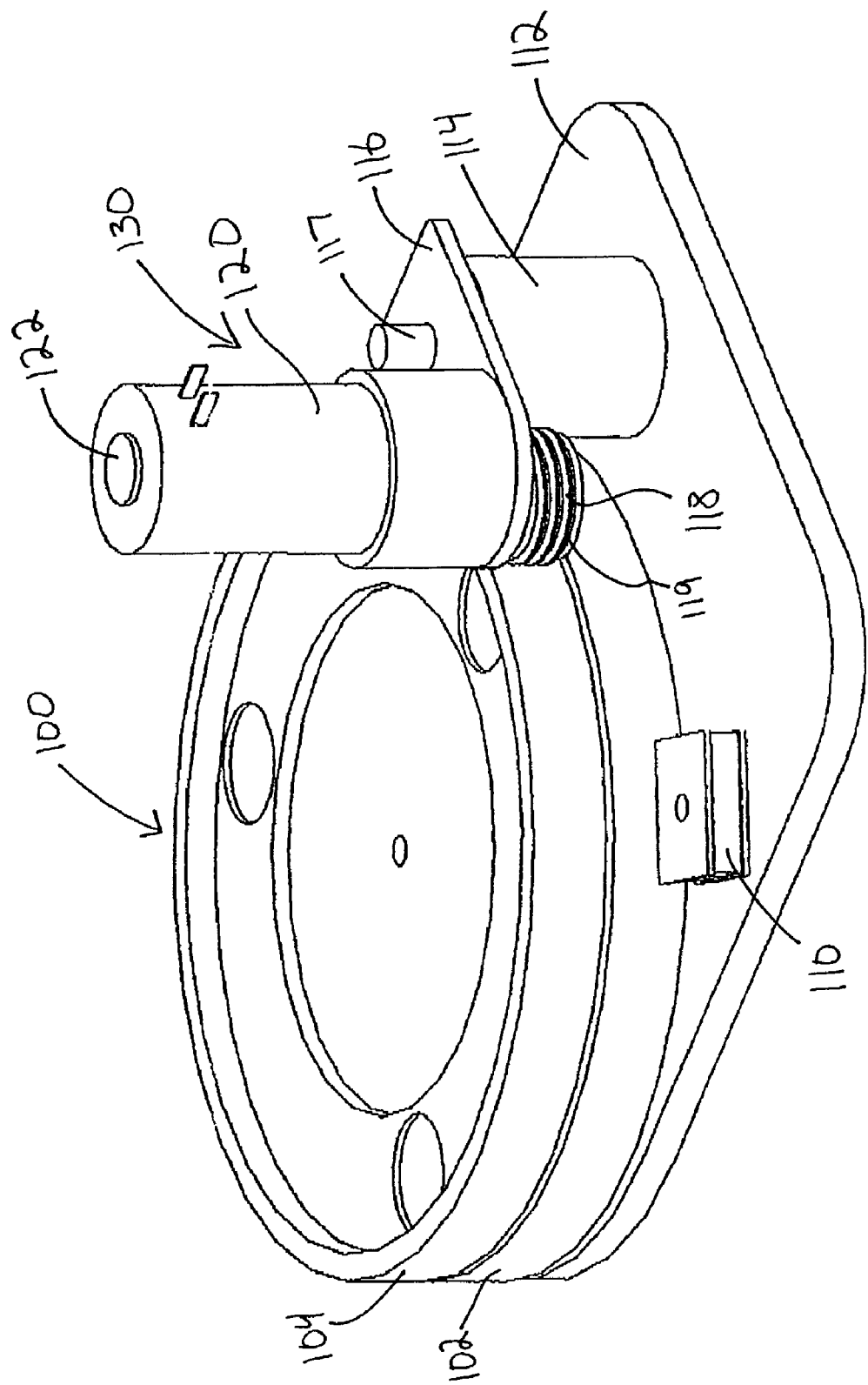
FIG. 5 is a perspective view of another embodiment of the present invention for rotating a conventional turntable 100.

FIG. 5 shows another embodiment of the present invention including a base plate 112 and actuator assembly 130 that operates in connection with a conventional turntable 100 for a petri dish. As FIG. 5 illustrates, turntable 100 rests on base plate 112 and against one or more stops 110 abutting against base 102 of turntable 100. Stops 110 may optionally be magnets to help hold turntable 100 in place. Actuator assembly 130, in one embodiment, comprises actuator base 114, arm 116, ring magnet 118 and motor 120. Ring magnet 118 is operably attached to the rotating shaft (not shown) associated with motor 120. The poles of the ring magnet 118, in one embodiment, abut against the outer surface of rotating plate 104 creating a magnetic force that attracts ring magnet 118 to rotating plate 104. Arm 116, in one embodiment, is pivotally attached to actuator base 114 at attachment point 117. As FIG. 5 illustrates, the pivotal attachment between arm 116 and actuator base 114 allows arm 116 to move to adjust to the outer surface (e.g., non-circular imperfections, bumps, other surface features, etc.) of rotating plate 104 as it rotates. In one embodiment, actuator base 114 is an integral part of base 112. In another embodiment, actuator base 114 is formed separately from base 112 and subsequently attached to base 112.

When motor 120 is actuated, ring magnet 118 rotates; the frictional force between ring magnet 118 and rotating plate 104 causes rotating plate 104 to spin. In one embodiment, ring magnet 118 includes grooves to accommodate O-rings 119 which rest against the outer surface of rotating plate 104 to improve the frictional contact between ring magnet 118 and the outer surface of rotating plate 104. In another embodiment, ring magnet 118 is coated with a rubberized or other suitable coating to improve frictional contact. However, other embodiments of the invention can be used merely with ring magnet 118 (i.e., metal-to-metal contact) and without such O-rings or coatings. As shown, the outer surface of magnetic ring 118 is substantially cylindrical; however, other suitable outer surface shapes can be employed as long as they provide sufficient contact to drive rotating plate 104.

As one skilled in the art will recognize, the use of magnetic ring 118 as described above assumes that turntable 100 (or at least rotating plate 104 or a portion thereof) is a magnetic/magnetizable material, such as (but not limited to) cast iron, steel or other ferrous materials. As discussed above, motor 120, in one embodiment, is a variable speed motor including knob 122 that is used to turn the motor on/off and adjust the speed of rotation.

Figure 6:
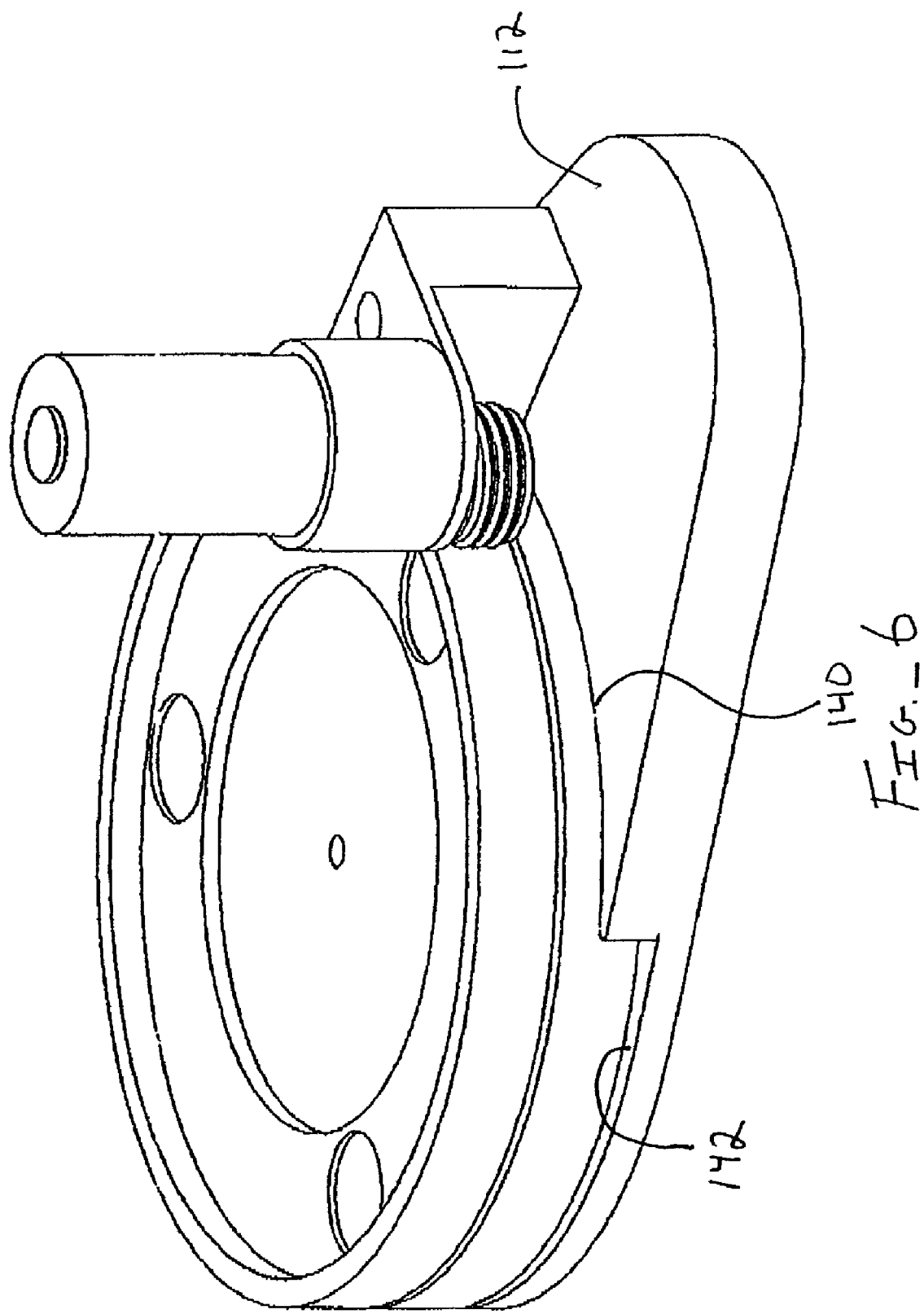
FIG. 6 is a perspective view of an embodiment of the present invention featuring a recessed surface and upper edge dimensioned to conform to a conventional petri dish turntable.
Figure 7:
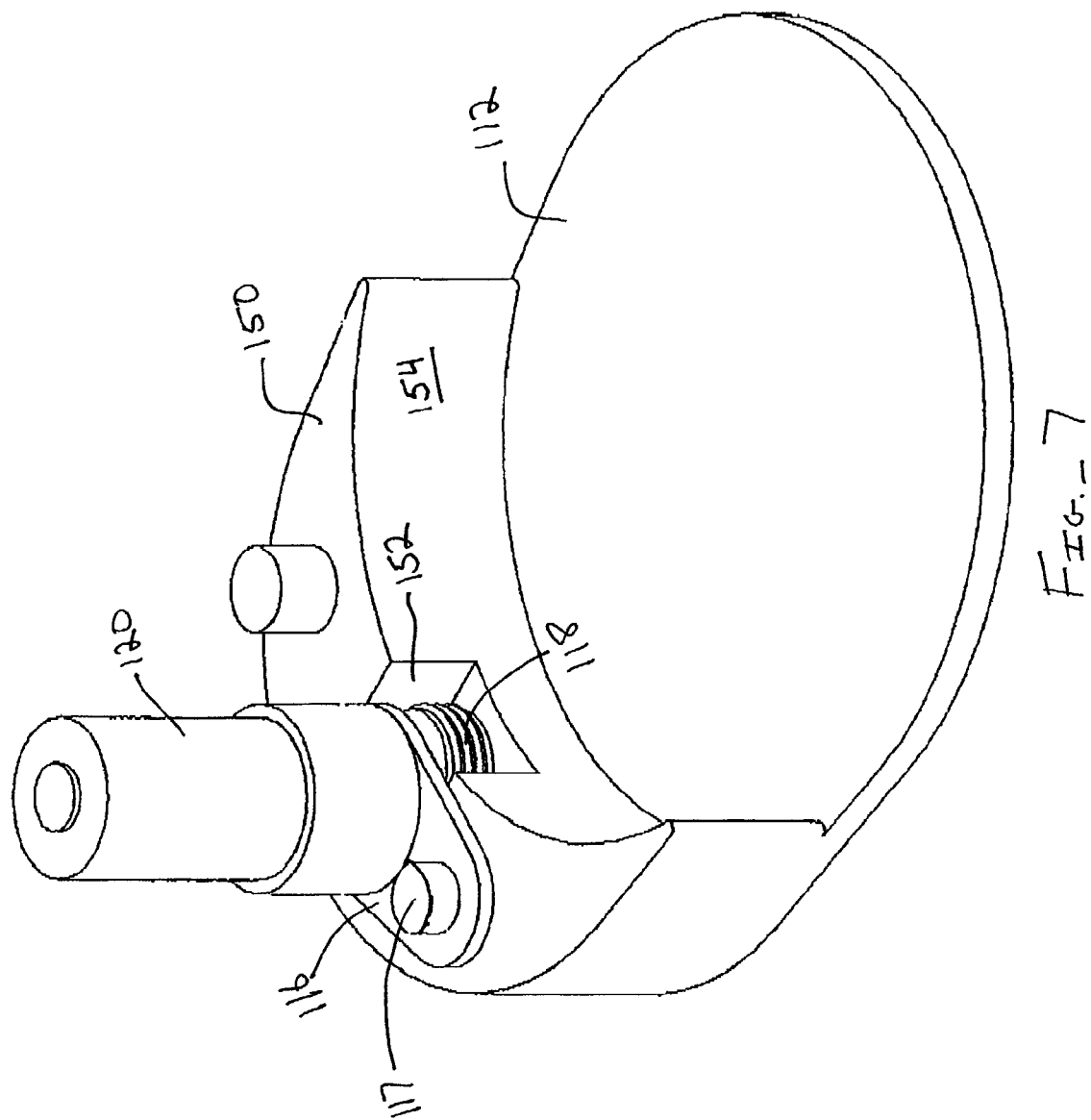
FIG. 7 is a perspective view of yet another embodiment of the present invention featuring a raised area including a recess in which the magnetic actuator moves.

FIGS. 6 and 7 illustrate alternative embodiments of the present invention. As FIG. 6 illustrates, base 112 may include recessed surface 142 on which turntable 100 rests with base plate 102 resting against edge 140. As FIG. 7 illustrates, base 112 may include raised area 150 including recess 152 and curved surface 154. Curved surface 154 substantially conforms to the outer surface of turntable 100. As FIG. 7 illustrates, magnetic ring 118 lies within recess 152. Arm 116 rotates about attachment point 117 to allow magnetic ring 118 to contact the outer surface of rotating plate 104 of turntable 100 as discussed above.

Lastly, although the present invention has been described with reference to specific embodiments, various other embodiments are possible without departing from the scope of the present invention. Other embodiments of the present invention will be apparent to one of ordinary skill in the art. It is, therefore, intended that the claims set forth below not be limited to the embodiments described above.

What is claimed is:

1. A stand-alone apparatus for use with a turntable that includes an upper plate rotatably attached to a base wherein a top surface of the upper plate is fitted to accept a petri dish, and wherein the upper plate and the base are both made from a magnetically-sensitive material, the stand-alone apparatus comprising:

a base plate including an upper surface for supporting the turntable one or more magnets extending from the upper surface of the base plate wherein the one or more magnets are adapted to apply a magnetic force releasably holding a portion of the base outer region of the turntable;

a rotating magnetic member positioned such that the rotating magnetic member will come into contact with an upper plate outer region when the portion of the base outer region of the turntable is releasably held by the one or more magnets, and wherein the upper plate rotates in an opposite direction as that of the rotating magnetic member when the rotating magnetic member rotates, and wherein the rotating magnetic member is rotatably attached to a first end of an arm, and wherein a second end of the arm is attached to the stand-alone apparatus; and means for rotating the rotating magnetic member.

2. The stand-alone apparatus as recited in claim 1 wherein the means for rotating the rotating magnetic member comprises a motor attached to the magnetic member.

3. The stand-alone apparatus as recited in claim 2 wherein the motor is a variable speed motor.

4. The stand-alone apparatus as recited in claim 3 wherein the variable speed motor is an electric variable speed motor.

5. The stand-alone apparatus as recited in claim 3 wherein the variable speed motor further comprises a switch assembly for actuating the variable speed motor.

6. The stand-alone apparatus as recited in claim 5 wherein the switch assembly comprises a switch knob attached to the stand-alone apparatus.

7. The stand-alone apparatus as recited in claim 5 wherein the switch assembly comprises a foot-operated pedal.

8. The stand-alone apparatus as recited in claim 1 wherein the rotating magnetic member includes a rotating non-magnetic member wherein the rotating non-magnetic member causes the turntable to move in an opposite direction as that of the rotating non-magnetic member, when the rotating non-magnetic member rotates, due to friction between the upper plate and the rotating non-magnetic member.

9. An stand-alone apparatus for rotating a turntable fitted to accept a petri dish comprising:
   a concavely-shaped inner region to match to and to come into contact with a portion of a base outer region of the turntable wherein the inner region includes a recess;
   a magnet adapted to apply a magnetic force releasably holding the turntable against the inner region;
   a rotating member, located in the recess, capable of rotating the turntable when an edge of the turntable comes into contact with the rotating member wherein the rotating member is rotatably attached to a fist end of an arm, and wherein a second end of the arm is attached to the stand-alone apparatus; and
   means for rotating the rotating member.

10. The stand-alone apparatus as recited in claim 9 wherein the rotating member is a rotating magnetic member.

11. The stand-alone apparatus as recited in claim 10 wherein the turntable is made from a magnetically-sensitive material.

12. The stand-alone apparatus as recited in claim 11 wherein the means for rotating the magnetic member comprises a motor attached to the magnetic member.

13. The stand-alone apparatus as recited in claim 12 wherein the motor is a variable speed motor.

14. The stand-alone apparatus as recited in claim 13 wherein the variable speed motor is an electric variable speed motor.

15. The stand-alone apparatus as recited in claim 13 wherein the variable speed motor further comprises a switch assembly for actuating the variable speed motor.

16. The stand-alone apparatus as recited in claim 15 wherein the switch assembly comprises a switch knob attached to the stand-alone apparatus.

17. The stand-alone apparatus as recited in claim 15 wherein the switch assembly comprises a foot-operated pedal.

* * * * *

UNITED STATES PATENT AND TRADEMARK OFFICE
CERTIFICATE OF CORRECTION

| | | |
|---|---|---|
| PATENT NO. | : 7,105,338 B1 | Page 1 of 1 |
| APPLICATION NO. | : 10/262995 | |
| DATED | : September 12, 2006 | |
| INVENTOR(S) | : Richard Holmes et al. | |

It is certified that error appears in the above-identified patent and that said Letters Patent is hereby corrected as shown below:

Column 5, line 27, change "An" to --A--

Signed and Sealed this

Eleventh Day of September, 2007

JON W. DUDAS
*Director of the United States Patent and Trademark Office*